United States Patent [19]

Coutts et al.

[11] Patent Number: 4,961,647

[45] Date of Patent: Oct. 9, 1990

[54] ORTHOPEDIC CEMENT MIXER

[75] Inventors: Garry D. Coutts, N. Syracuse, N.Y.; Eugene P. Lautenschlager, Skokie, Ill.; Richard L. Wixson, Evanston, Ill.; Michael A. Novak, Morton Grove, Ill.

[73] Assignee: DHD Medical Products, Canastota, N.Y.

[21] Appl. No.: 243,216

[22] Filed: Sep. 12, 1988

Related U.S. Application Data

[63] Continuation of Ser. No. 848,214, Apr. 4, 1986, abandoned.

[51] Int. Cl.⁵ ............................................. B01F 7/20
[52] U.S. Cl. .................................... 366/139; 366/247; 366/309; 366/325
[58] Field of Search .................. 366/139, 248, 64, 67, 366/309, 341, 229, 244, 245, 247, 325, 330, 343, 602

[56] References Cited

U.S. PATENT DOCUMENTS

| 414,566 | 11/1889 | Nelleson | 366/309 |
|---|---|---|---|
| 740,751 | 10/1903 | Friedman | 366/307 |
| 1,023,368 | 4/1912 | Fry | 366/245 |
| 1,033,667 | 7/1912 | Brown | 366/296 |
| 1,181,869 | 5/1916 | Gerbing | 366/325 |
| 1,415,735 | 5/1922 | Trust et al. | 366/309 |
| 2,347,195 | 4/1944 | Huff | 366/330 |
| 2,696,022 | 12/1954 | Steinbock et al. | 366/111 |
| 2,973,187 | 2/1961 | Wehmer | 366/279 |
| 3,249,969 | 5/1966 | Steinbock, Jr. | 425/207 |
| 3,342,460 | 9/1967 | Bolde | 366/251 |
| 3,635,901 | 1/1972 | Urgesi et al. | 366/325 |
| 4,020,154 | 4/1977 | Perla et al. | 424/49 |
| 4,069,310 | 1/1978 | Harrison | 424/49 |
| 4,185,072 | 1/1980 | Puderbaugh et al. | 366/248 |
| 4,277,184 | 7/1981 | Solomon | 366/139 |
| 4,380,399 | 4/1983 | Godat et al. | 366/309 |
| 4,438,074 | 3/1984 | Wilt | 366/172 |
| 4,460,279 | 7/1984 | Krasney | 366/247 |
| 4,462,694 | 7/1984 | Ernster et al. | 366/314 |
| 4,488,817 | 12/1984 | Jesaka et al. | 366/293 |
| 4,586,823 | 5/1986 | Schöndorfer et al. | 366/325 |
| 4,721,390 | 1/1988 | Lidgren | 366/139 |

FOREIGN PATENT DOCUMENTS

| 1193479 | 5/1965 | Fed. Rep. of Germany | 366/330 |
|---|---|---|---|
| 627769 | 10/1927 | France | 366/330 |

OTHER PUBLICATIONS

Written Opinion regarding PCT/US 87/00895 application, dated Apr. 17, 1989.

Primary Examiner—Harvey C. Hornsby
Assistant Examiner—Joseph S. Machuga
Attorney, Agent, or Firm—Cushman, Darby & Cushman

[57] ABSTRACT

A combination mixing and reacting device for mixing cement used in orthopedic procedures capable of operating under partial vacuum conditions in order to permit the simultaneous deaeration and blending of cement components to produce a fully mixed porosity free cement mixture. The device includes a mixing vessel and a reinforced evacuable housing as well as an improved mixing paddle design operable from outside the device that efficiently and appropriately allows this mixing and deaeration to continue.

19 Claims, 6 Drawing Sheets

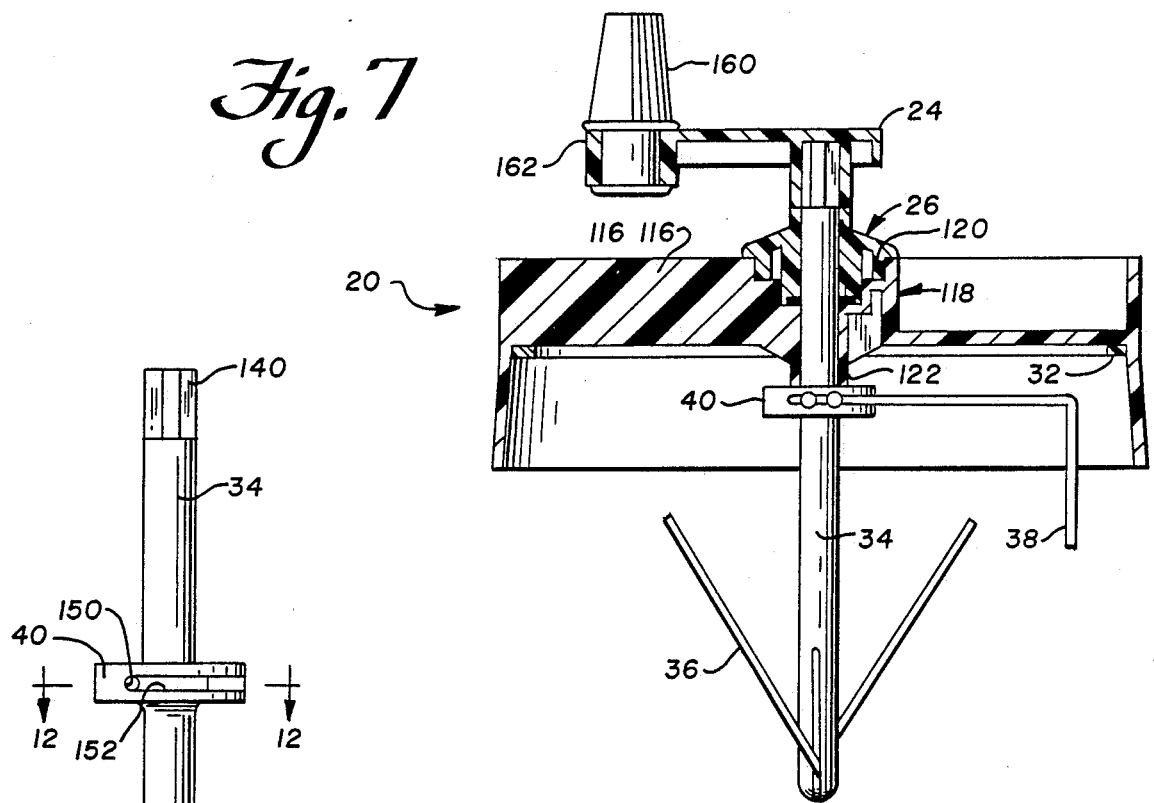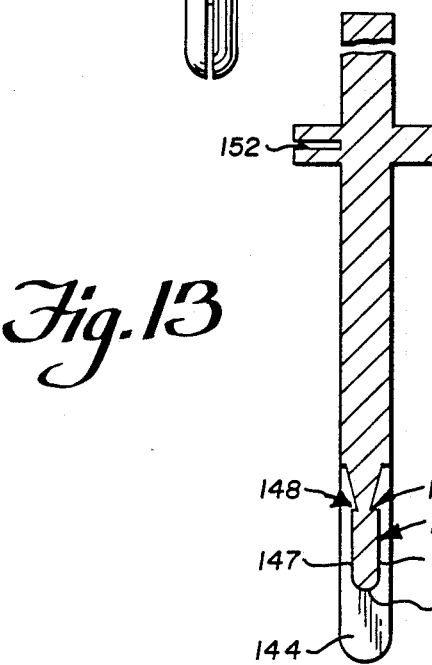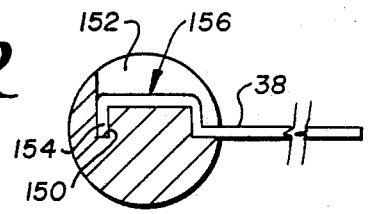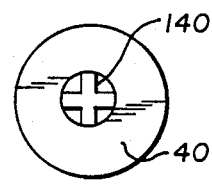

ORTHOPEDIC CEMENT MIXER

This is a continuation of application Ser. No. 06/848,214, filed Apr. 4, 1986, which was abandoned upon the filing hereof.

FIELD OF THE INVENTION

Present invention relates to apparatus for blending liquid and dry reactants to form products for use in orthopaedic surgical procedures.

BACKGROUND AND BRIEF DESCRIPTION OF THE INVENTION

A known type of low vacuum orthopaedic cement mixer is described in Puderbaugh et al, U.S. Pat. No. 4,185,072, which operates at very low vacuum levels ranging from 80 to 120 mm of mercury in order to remove the monomer vapor fumes and the odor associated therewith from the surgical suite during mixing. Prior to this, mixing was accomplished by hand spatulation using a paddle in an open vessel.

It is well known that in many orthopedic surgical procedures it is necessary to employ a cement or grouting type agent, such as for attaching artificial joint implants, repairing or forming joints in bones, or other forms of orthopaedic work. The type of cement generally used for these purposes are self-curing resins formed from the blending of a wide variety of liquid monomers or comonomers with powdered polymers or copolymers to form a viscous admixture to be used as the grouting agent. When set, the resulting cements contain poly(methyacrylic acid esters) as their main ingredient. The powder, and subsequently the cement, can also contain such things as radiopacifiers, antibiotics, plasticizers, crosslinking agents, and compositing reinforcing fibers or beads.

The admixture of the powder and liquid components develops a quick setting material and preparation of the cement usually occurs directly within the operating theater just prior to use. This mixing must occur rapidly so the viscous admixture can be utilized in the orthopaedic procedure before autopolymerization occurs and the cement sets hard.

In the powder component, which can be an air-fluffed powder, air (upward of 50 percent by volume) is usually desirable around the powder particles to readily enable the liquid to wet the powder. We have recognized that if this necessary air is not subsequently removed from the viscous admixture, it will end up as small to medium sized pores within the set cement. Prior to the present invention removal of air or deaeration of the cement was not possible.

There are a number of sources of air bubbles within the cement admixture, such as from the air present in the powder component which can become entrapped upon blending with the liquid, or when the admixture becomes lumpy during mixing and the lumps themselves coalese thereby allowing bubbles to be formed there between. The dragging or moving of the paddle through the mixture also can create bubbles within the mix due to folding in of external air as was found to be the case with known paddle designs. Moreover, known paddle designs may cause the small and medium bubbles to coalesce into large bubbles. Also bubbles of monomer vapor may be present in the admixture.

The cement must be uniformly and thoroughly mixed in a relatively short amount of time so as to be as homogenous as possible and, preferably, without any entrapped gas in the form of air or monomer vapor. Mixing of the cement components may incorporate gas within the mixture. This entrapped gas will have to be removed in order to subsequently develop a set cement product that is not porous and exhibits desirably increased static and dynamic mechanical strengths.

We prefer to remove as much of the entrapped gas from the mixture as mixing proceeds as is possible so that few, if any, entrapped bubbles will remain within the viscous admixture thereby also eliminating porosity in the set cement. Were such bubbles to remain within the mixture, the mechanical properties of the set cement would not be as desired and a fracture might develop in the hardened cement at the points where such bubbles, entrapped air spaces or pores were located. Also, because some monomer vapor fumes might be generated which can be noxious and/or toxic in nature, and because mixing can often be carried out for a period of several minutes to assure a uniform mixture, it is desirable to filter the gas being removed.

The present invention is primarily concerned with a device that will more thoroughly mix the components under partial vacuum conditions of approximately 550 mm of mercury which provides the ability to deaerate or remove incorporated gas both from the spaces between powder particles prior to blending as well as from the mixing components during blending. The invention employs a mixing paddle designed to avoid dragging gas bubbles through the as mixing proceeds. Further, following initial blending, and with continued back and forth movement in clockwise and counterclockwise directions, the paddle interacts with the mixing components and creates flow and mixture movement conditions within the mixing vessel that aids the removal of any remaining gas bubbles. The mixing blades, when moved through the components, develop very large exposed surface areas within the mixture against which gas bubbles can be brought and there burst. The present invention also necessarily contemplates device that can withstand substantially higher vacuums than has heretofore been desirable.

The present invention is comprised of a modified reaction-mixing vessel, from that described in Puderbaugh et al, having an outer housing that is substantially reinforced in order to withstand high vacuums, a modified sealing cover structure, and a greatly modified mixing paddle. The apparatus described in Puderbaugh et al required use of an air vent or a loose fitting lid so that the interior of the reaction-mixing vessel would receive enough of an air flow so that excessive vacuum conditions within the apparatus would specifically be avoided. The present invention seeks just the opposite, that is, to provide a reaction-mixing vessel in which it is possible to develop a high partial vacuum and the avoidance of leaks of outside air therein.

Additionally, it has been found that the mixing blades, beaters or vanes used in prior art devices have not suitably mixed the materials nor have they handled or manipulated the components being mixed within the mixing chamber such that the mixture could be exposed, to the greatest extent possible, to the partial vacuum conditions within the mixing chamber. Further, prior mixing devices did not develop a circulation flow path that would move the mixing components upward and downward in the center of the mixing chamber, nor radially relative to the sidewall or along the sidewall of the mixing device, all of which assist in deaerating the viscous admixture.

After the liquid has been placed in the mixing vessel and the powder admixed into that liquid, wetting will have begun but some of the powder will continue to float on the liquid surface. By applying a partial vacuum after closing the vessel, some of the entrapped gas within the floating powder, but not all, will be removed.

For the entrapped gas bubbles incorporated within the mixed components to be removed, the pores or bubbles must be broken by the paddle structure or opened by vacuum conditions within the mixing vessel. In order for this to be accomplished the bubbles must be brought very close to or exposed on an exposed surface of the admixture. At the same time, it is not desirable to create larger pores or bubbles. Mixing blades that will cause or allow small gas bubbles to coalesce into larger bubbles will not aid in ridding the mixture of bubbles and might well further degrade the mechanical properties of the set cement product. It was found to be necessary, therefore, that large surface areas of the mixture be continuously developed and reformed during mixing so that entrapped or incorporated bubbles will be brought to an exposed surface of the mixture. When that occurs the entrapped gas bubbles can burst either by action of the mixing device or by exposure to the relatively high vacuum conditions within the vessel. It must also be understood that the vacuum level is preferably controlled to lie within a desired optimal range of about 500 to about 600 mm of mercury. If the applied vacuum is too low the porosity-causing gases cannot be effectively removed from the viscous admixture. Conversely, if the vacuum is too high, the liquid monomer will boil and create additional porosity problems.

The mixing paddle has a unique design and creates specific flow patterns within the mixture, depending upon the direction of rotation, which can occur in both clockwise and counterclockwise direction. The paddle provides not only much better mixing but a circulating flow which assures that, to the greatest extent possible, large and continuously changing surface areas of the mixed components become exposed to the vacuum conditions within the reaction-mixing vessel so that bubbles otherwise entrapped throughout the mixture will themselves be exposed and the gas released. Further, the paddle structure will not coalesce or merge the bubbles together as mixing progresses but rather allows the incorporated gas in the form of small bubbles to be treated equally as well as large bubbles.

The mixing device herein is designed to mix a variety of types of bone cements such as, for example, the mixing of self-curing resins used primarily for the internal orthopedic endoprostheses, as may be produced from the blending of a wide variety of monomers or comonomers with polymers or copolymers, which may produce polymethacrylic acid esters as the main ingredient in the set cement.

The mixer has also been designed to mix different quantities of bone cement, that is, single batches and double batches, not uncommonly 50 grams to 120 grams of admixture of said bone cement.

Other objects, features, and characteristics of the present invention, as well as the methods and operation and functions of the related elements of the structure, and to the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 7 is a cross-sectional view of the cover with the paddle and hand crank in place;

FIG. 11 is a side elevational view of the mounting post for the paddle;

FIG. 12 is a cross-section taken along the lines 12—12 and FIG. 11;

FIG. 13 is a cross-section of the mounting post shown in FIG. 11;

FIG. 14 is a top plan view of the mounting post shown in FIG. 11;

FIG. 18 is a top plan view of the bottom plate of the mixing vessel as shown in FIG. 4a.

DETAILED DESCRIPTION OF THE PREFERRED EXEMPLARY EMBODIMENT OF THE PRESENT INVENTION

Figure 1:
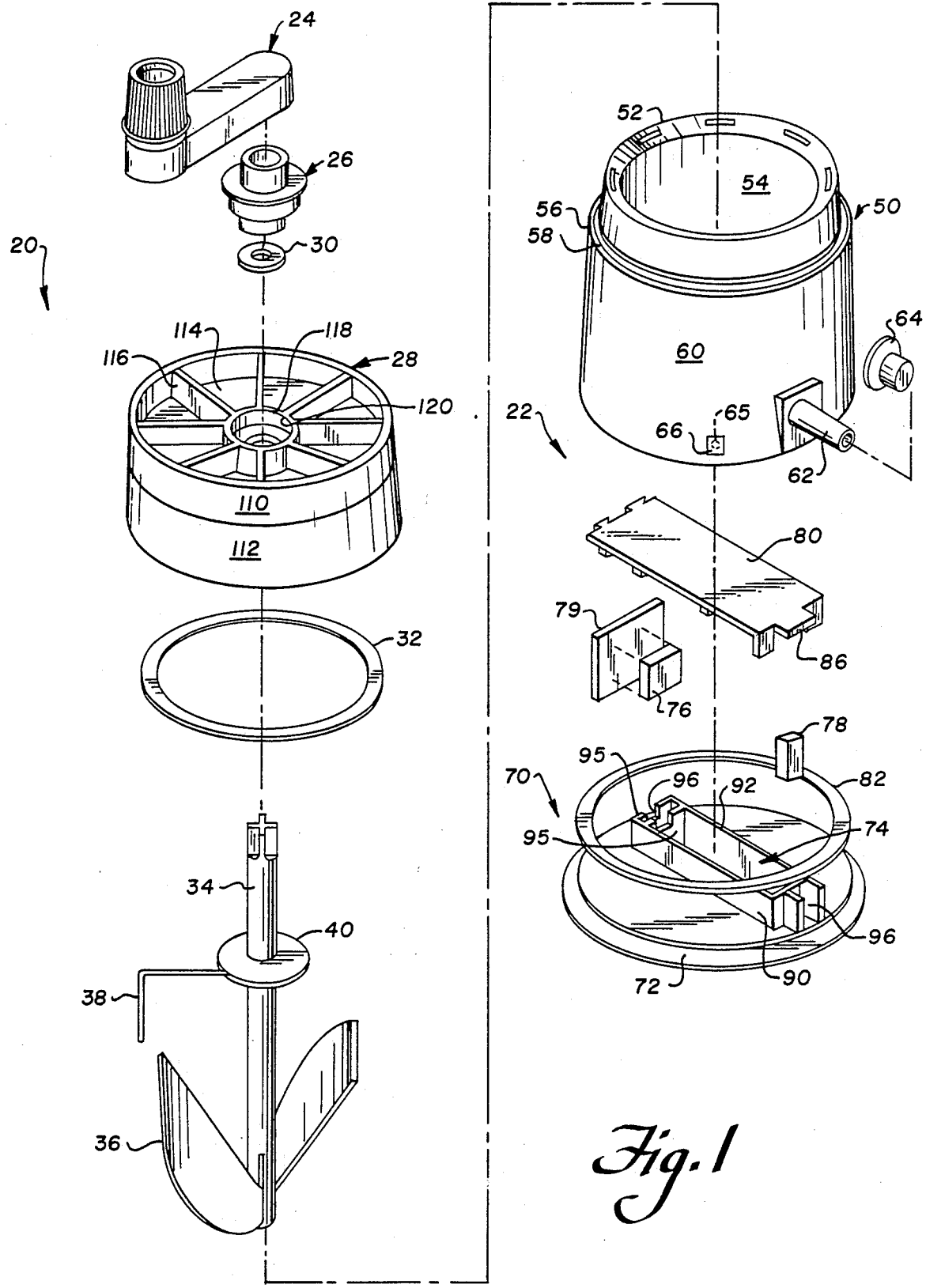
FIG. 1 is an exploded perspective view of the device constituting the present invention.

With reference to FIG. 1, the present device is comprised of a cover assembly 20, and a reaction-mixing vessel assembly 22.

Figure 4A:
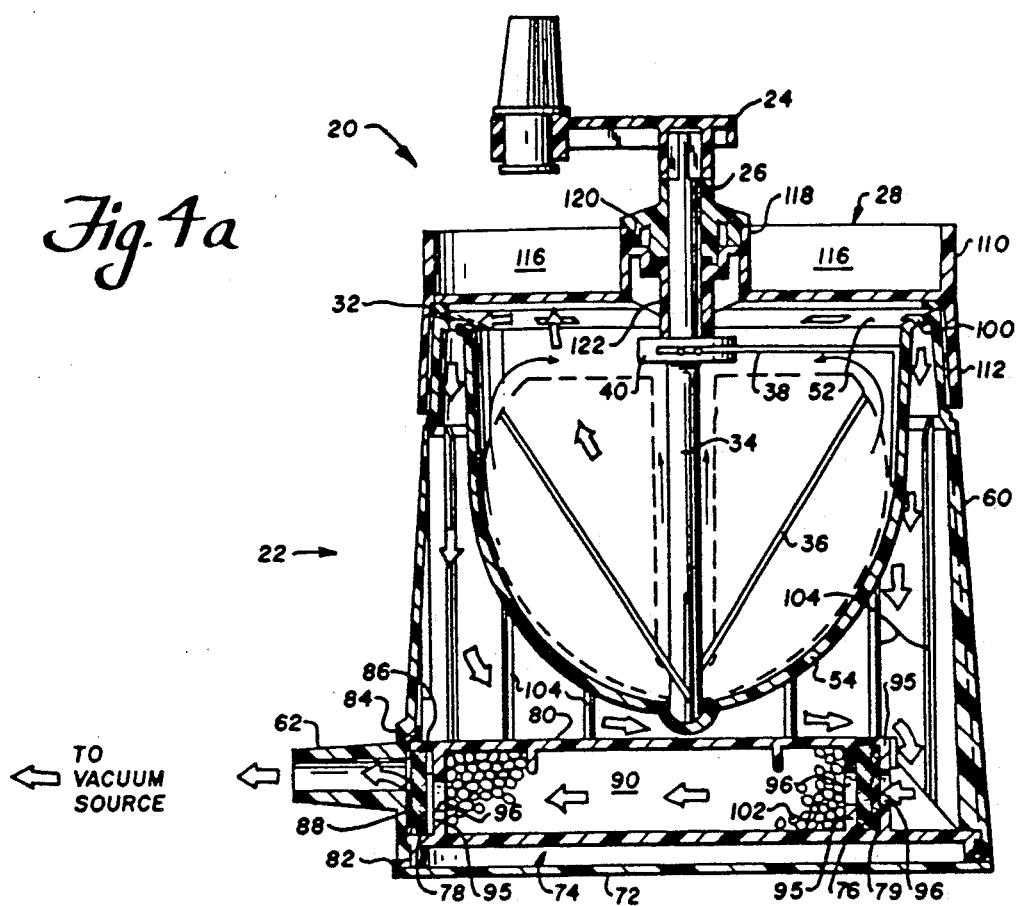
FIG. 4a is a cross-section of the device as shown in FIG. 1.

Cover assembly 20 is comprised of a handle or hand crank 24 which mates with a bushing 26, the latter fitting within cover member 28, the seal there between being provided by a sealing washer 30. A rubber or foam gasket 32 is provided on the interior periphery of the cover, as is shown in FIG. 4a, where the left-hand sidewall cover has been broken away for clarity in order to show gasket 32. The cover remains intact on the right-hand side of that figure.

Cover assembly 20 also includes a subassembly in the form of a spindle support post 34 the upper portion of which extends through member 28 and bushing 26 to be fixed to handle 24. The lower end of post 34 serves to provide a mounting area to support a twin bladed mixing paddle 36. A separate metal stirrer 38 extends outwardly from an integral flange 40 on post 34 and when assembled that flange will engage the bottom of cover 28 as in FIG. 4a.

The reaction-mixing vessel assembly 22 is comprised of an outer housing 50 having a bevelled upper rim 52, an interior concave mixing bowl or chamber 54, an outer upper edge having a tapered outer sidewall 56 adjacent rim 52 that terminates at a shoulder 58 that extends substantially horizontal to wall 56, and a tapered outer lower side wall 60 that extends downwardly from shoulder 58. A vacuum connecting nozzle 62 is provided adjacent the base of housing 50, and a cap 64 can be provided to close nozzle 62 in order to maintain sterile conditions. Except for cap 64, these mixing vessel elements are preferably integrally formed by conventional in section molding. In order to provide an alternative way to vent the mixing vessel following mixing, rather than introducing the vacuum hose (not shown), a separate vent 65 can be provided in sidewall 60, adjacent nozzle 62 with that vent being covered with a removable tape 66.

The reaction-mixing vessel assembly 22 also includes a base assembly 70 comprised of a planer bottom member 72 on which a rectangular housing 74 including a separate cover 80 is provided for enclosing a filter. The filter includes porous or open cell foam pads 76 and 78 located at opposite ends of the housing, each part having a porosity of about 100 pores per lineal inch (ppi). An anti-blowback, hydrophobic filter 79 is provided between pad 76 and the interior of housing 50. This anti-blowback filter preferably has a pore size of about 0.8 microns, is formed from an acrylic material to prevent charcoal fines from the charcoal absorption medium 102 from blowing back interiorly toward the mixture when the vacuum is released prior to removing the cover following mixing. In addition, a rubber or foam gasket 82 is provided to develop a seal between the planer bottom member 72 and housing 50.

It should be understood that post 34 and flange 40 are preferably formed as an integral unit, and that housing 50 together with the concave mixing bowl 54, and sidewalls 56 and 60 and nozzle structure 62 are likewise formed as an integral unit. The planer member 72 and housing 74 attached thereto can either be separately formed as an integral unit or the wall structure comprising 74 itself can be separately formed and secured to the planer member 72 by any convenient means such as, for example, by glue or by a conventional heat sealing process.

Figure 2:
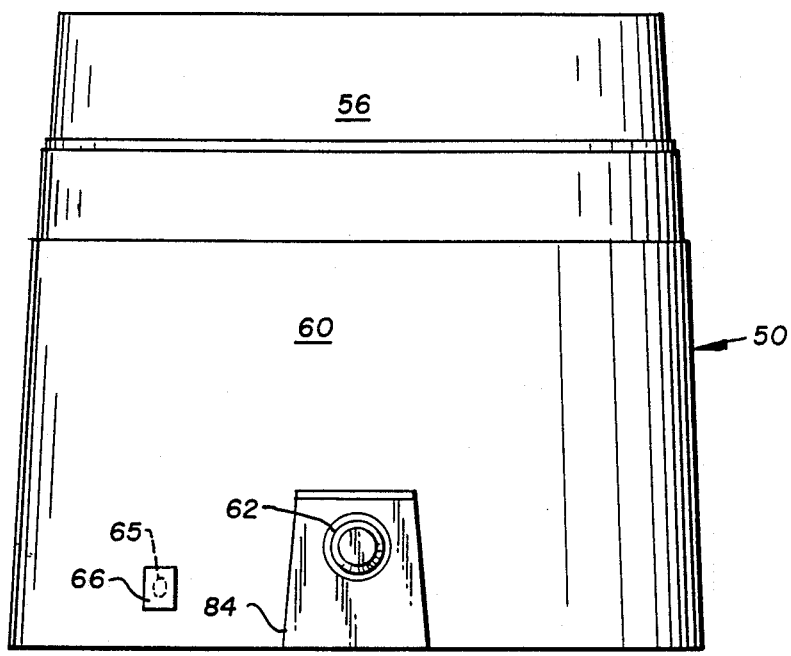
FIG. 2 is a front elevational view of the reaction-mixing vessel.

With reference to FIG. 2, the area at the base of nozzle 62 is enlarged, as indicated at 84, so that it extends outwardly from sidewall 60, and is similarly shaped interiorally thereof The shape of this portion 84 can be either rectangular or slightly trapezoidal, and in either case is designed to provide a similarly shaped interior recess in which the front portion of housing 74 and top 80 will be received If desired, an additional sealing gasket 88, shown in FIG. 4a, can be placed within this recess to seal about the portion of housing 74 received there against as well as a forwardly projecting tongue 86 provided on the top member 80, as shown in FIG. 1, which will fit within the top horizontal section of the enlarged area 84. This is shown in its assembled form in FIG. 4a.

Housing 74 is comprised of a pair of upstanding spaced apart sidewalls 90 and 92 with a pair of spaced apart endwalls 95 at each end to define a retaining groove 94 there between for respectively holding filter pads 76 and 79 in place at the rear end and filter pad 78 at the front end, as shown in FIG. 4a.

Figure 3:
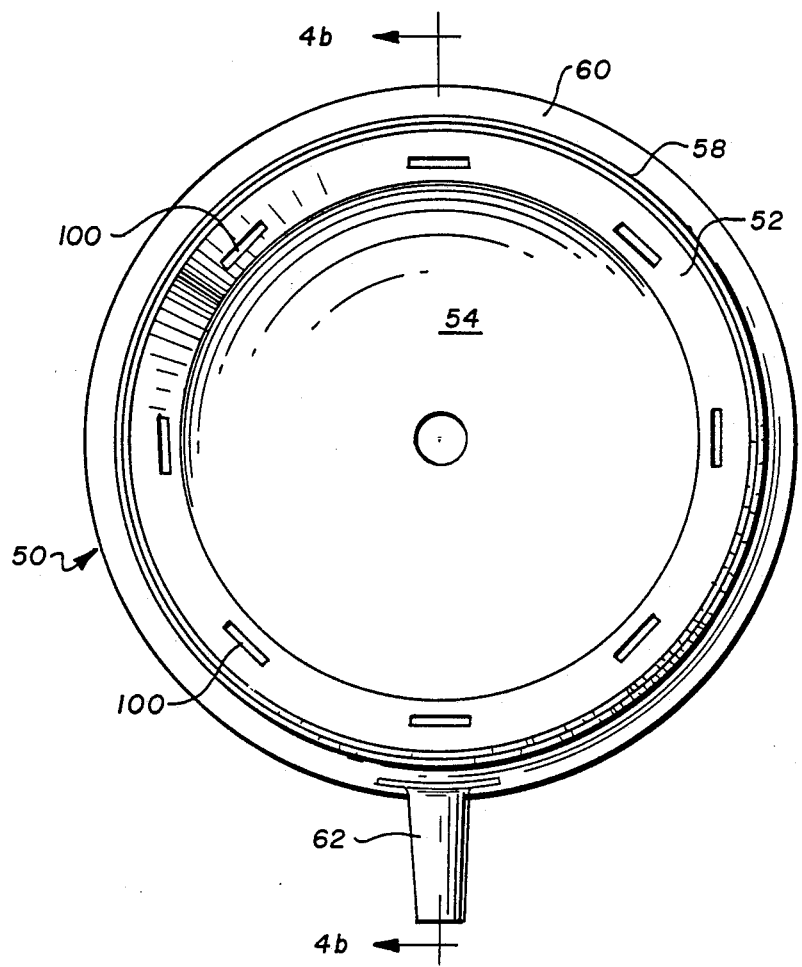
FIG. 3 is a top plan view of the reaction-mixing vessel shown in FIG. 2.
Figure 4B:
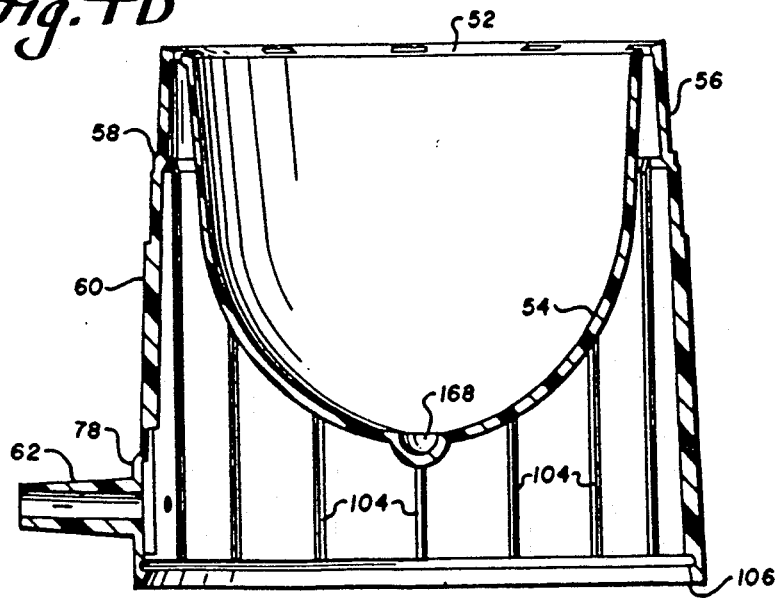
FIG. 4b is a cross-section taken along lines 4b—4b of FIG. 3.
Figure 5:
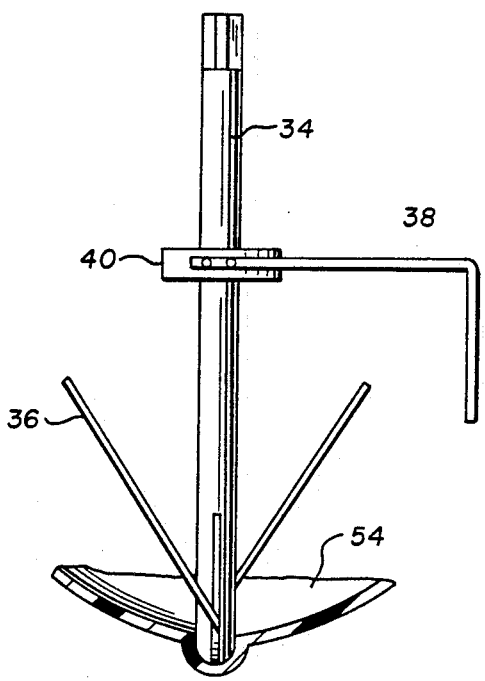
FIG. 5 is an elevational view of the paddle of the present invention without the handle thereon and showing a portion of the reaction-mixing vessel in cross-section.

Thus, the entire filter structure is comprised of the porous foam pads 76 and 78, anti-blow back filter 79 and the body of absorption material 102 comprised of charcoal or other conventional gaseous absorption material. Endwalls 95 are also provided with cut-out portions or apertures 96 to provide a clear passage through the filter. As shown in FIG. 4, one end of the housing 74 is positioned adjacent the interior of nozzle 62 against gasket 88, with the other end being exposed to the area within housing 50 and spaced interiorally of wall 60. As shown in FIG. 3, the bevelled or sloping surface 52 is provided with a plurality of vents or apertures 100 which provide access to the evacuation chamber formed between housing 50, the exterior of the mixing bowl 54 and above base assembly 70. During use, incorporated air or gases generated by the reaction between the admixture of cement components within the reaction-mixing vessel 54 will be drawn through vents 100 and into the housing between the exterior of vessel 54 and the interior of housing 50, toward the rear of housing 74 and into and through the filter, finally exiting through nozzle 62 into a vacuum apparatus (not shown). If it is not desired to provide for such filtration or absorption, then the charcoal or absorptive material 102 in the filtering unit could be dispensed with. However, in most instances absorptive filtration is desirable.

In order to provide internal strengthening for housing 50, and in particular to wall portion 60, internally projecting ribs 104 are provided so that they extend from a position substantially adjacent the bottom edge 106 up to the base of wall 56. These internal ribs, preferably spaced about ¾ of an inch apart about the interior circumference of housing 50, are integrally formed together with the housing and prevent those walls from collapsing inwardly once vacuum is applied to the evacuation chamber formed above planer surface 72, and between wall 60 and mixing vessel 54.

Figure 6:
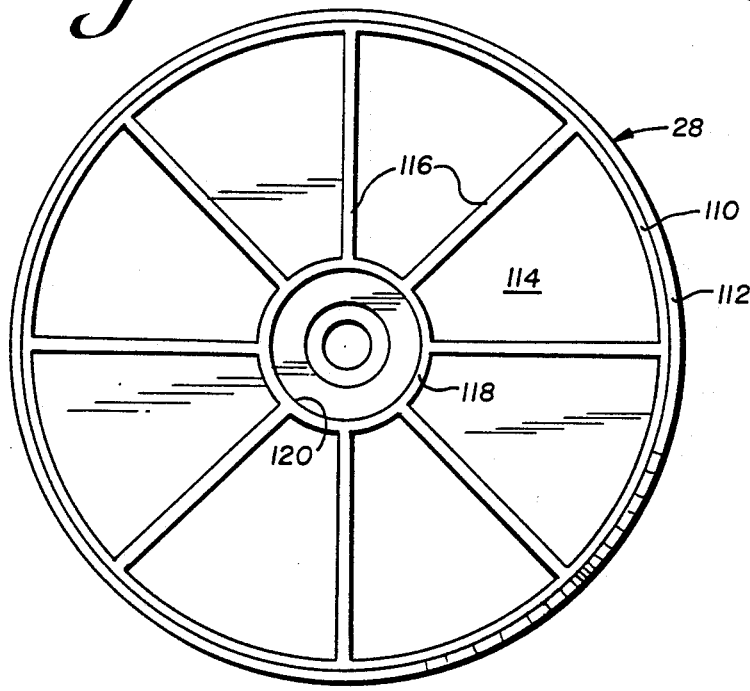
FIG. 6 is a top plan view of the cover as shown in FIG. 1.

With reference to FIGS. 1 and 6, cover 28 is provided with an upstanding cylindrical portion 110 forming the outer periphery of the cover from which a depending tapered portion 112 extends. An internal planer surface 114 extends across the interior of the circumferential portion 110 adjacent the juncture of portions 110 and 112, and a plurality of upstanding spaced apart, radially directed ribs 116 are provided on that planer surface. Each of these ribs terminates at...an, interiorally positioned, upstanding cylindrically shaped wall 118, the interior of which is formed with a cylindrically shaped recess or bore 120 from which a cylindrical sleeve 122 depends. The internal diameter of sleeve 122 is less than the internal diameter of recess 120 and is sized to rotatably receive post 34 therein.

Figure 8:
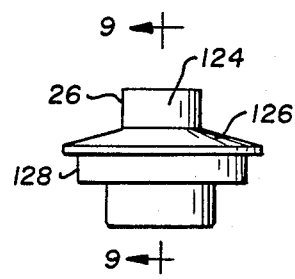
FIG. 8 is a side elevational view of the bushing used to seal about the paddle on top of the cover.
Figure 9:
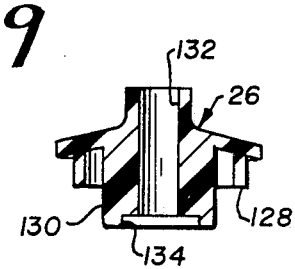
FIG. 9 is a cross-sectional view taken along line 9—9 in FIG. 8.
Figure 10:
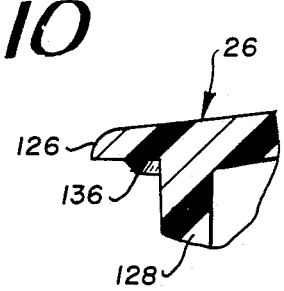
FIG. 10 is an enlarged cross-sectional view of a portion of the rim of the bushing shown in FIG. 9.

With reference to FIGS. 8–10, bushing 26 is provided with an upstanding collar portion 124 from which a sloping flanged surface 126 extends. A cylindrical shaped sleeve 128 extends from the bottom of flange portion 126, and as shown in FIG. 9, sleeve 128 spaced from a parallel depending cylindrical portion 130. A cylindrical bore 132 is provided centrally within the bushing 26, and an annular groove 134 is provided in the bottom portion 130 so as to be co-axially aligned with bore 132. With reference to FIG. 10, it can be noticed that a depending sealing rib 136 is spaced outwardly from sleeve 128 and depends from an extended portion of flange 126. Rib 36 can ultimately be glued or welded onto the cover and specifically onto a shoulder provided on the top edge of cylindrical portion 118. The sealing arrangement is shown both in FIGS. 4a and 7.

Turning now to FIGS. 11-14, the paddle support post 34 includes a main cylindrical shank with the upper end being provided with four shaped ribs 140, which will be received in a depending cylindrical sleeve 142 forming part of one end of handle 24. Handle 24 can be either heat sealed, glued or attached by any other convenient means to the top of post 34 so long as that connection is securely made.

The bottom portion of post 34 is provided with an downwardly opening slot 144, the interior of which includes a shaped core 146 having a rounded lower edge 145 from which two vertical sidewalls 147 extend upwardly so that each terminates at an to define two interior horizontal ledge 148 on each side of the core portion to act as catches for a spring clip provided on the paddle, as will be described below.

Collar 40 is provided with an aperture 150 that extends tangentially with respect to post 34 and opens out into a groove 152 which extends part way around the outer circumference of collar 40. As shown in FIG. 12, the metal stirrer 38 has an interior end 154 that will be heat staked into aperture 150, with a substantially U-shaped portion 156 of that stirrer being retained within groove 152. Stirrer 38 is comprised of a piece of 0.030 inch diameter, full hard, stainless steel music wire and will serve to scrape the interior sidewall of mixing chamber 54 above paddle 36 as shown in FIG. 4a as the handle 24 and post 34 are rotated.

With reference to FIG. 7, handle 24 includes a knob 160 rotably mounted within a cyclindral sleeve 162 at the end of the handle opposite sleeve 142. On operation, handle 24 can be turned clockwise and counter clockwise to inturn rotate the mixing paddle 36 in similar directions. It should be understood that a variety of types or arrangements could be employed to rotate paddle 36 and could, for instance, comprise a gear system, or some other indirect drive, or even some type of alternating direction power drive system.

When cover assembly 20 is fully assembled, as shown in FIG. 7, handle 24 will be secured to the top end of post 34 which extends upwardly cyclindral sleeve 122 with bushing 26 being retained in between and forming a seal together with gasket 30 about shaft 34. It will also be noticed that collar 40 preferably abuts the lower surface of sleeve 122. Thus, when cover assembly 20 is in place on housing 50, the depending tapered outer sleeve 112 will extend over a similarly tapered sidewall 56 with the interior surface of sleeve 112 abutting the exterior of sidewall 56. Gasket 32 will provide a further seal about the exterior of the upper edge 52 but radially outwardly of apertures 100 and assures the formation of the desired vacuum within the mixing chamber while allowing gas circulation out of apertures 100 once the vacuum source is applied. It should also be noted that the outer periphery of edge 52 can be flattened where it is to be in contact with gasket 32.

The preferred level of vacuum is about 550 millimeters of mercury with the preferred range being between 500 and 600 mm of mercury. Gasket 30 together with the other associated components in the handle and post structure will seal the area about the post while allowing the paddle structure to be rotated. Accordingly, when vaccum is applied through nozzle 62 it will be possible to effectively evacuate the area within the reaction-mixing vessel 54.

Post 34 can have a length of approximately 4.165 inches and a diameter of about 0.250 inches. Collar 40 can have a diameter of about 0.750 inches with the slot 144 being about one inch in length, with ledges 148 being positioned about 0.200 inches down from the top of the slot and having a horizontal length of about 0.023 inches.

Figure 15:
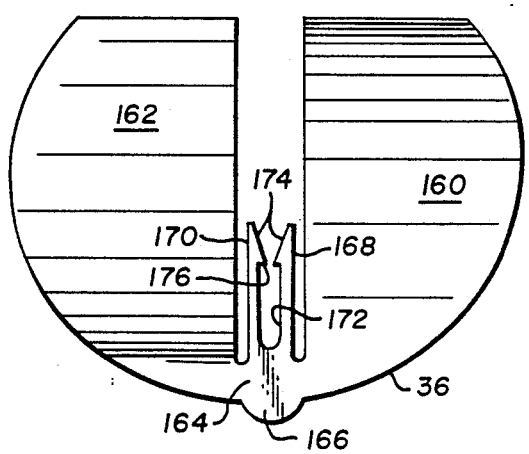
FIG. 15 is a front elevational view of the paddle shown in FIG. 1.
Figure 16:
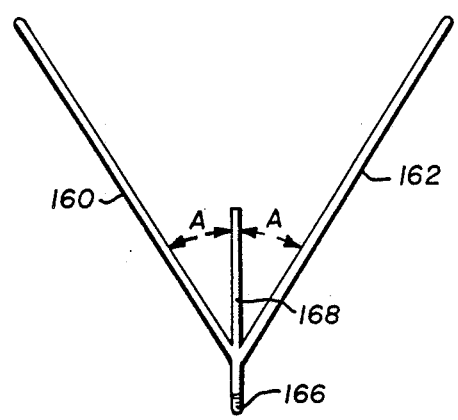
FIG. 16 is a side elevational view of the paddle shown in FIG. 15.
Figure 17:
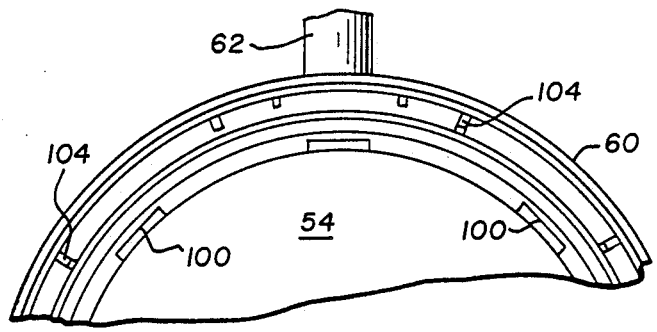
FIG. 17 is a partial bottom plan view of the mixing vessel as shown in FIG. 2.
Figure 18:
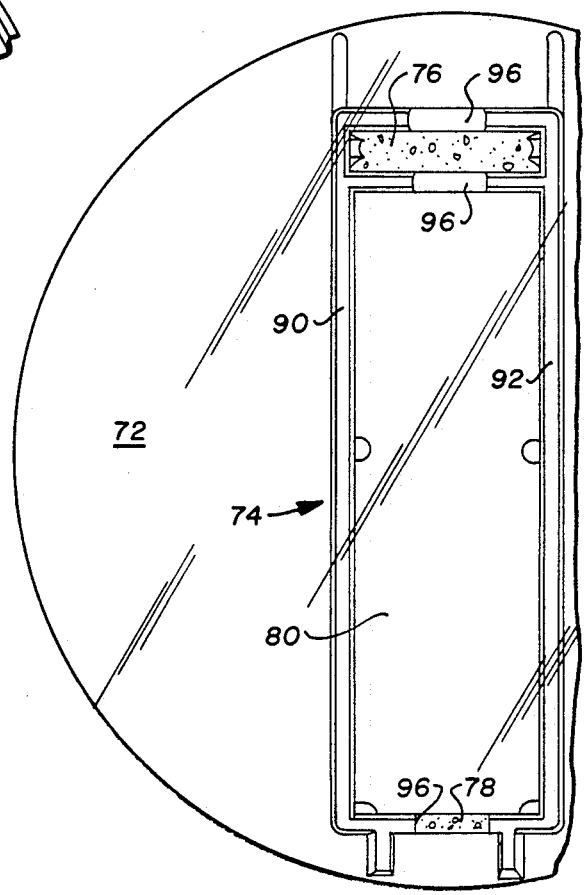

Turning now to FIGS. 15 and 16, paddle 36 is comprised of two paddle vanes 160 and 162, which are joined together by bridging portion 164. This bridging portion 164 has a depending lobe 166 that will fit within a concave depression 168 provided at the base of the reaction-mixing vessel 154, thus stablizing the stirring structure within the vessel. Extending upwardly from bridging section 164 is a spring clip comprised of two spaced apart spring members 168 and 170 having a shaped interior 172 corresponding to the shaped core portion 146 on post 34. In addition, spring members 168 and 170 are each provided with a sloped interior leading edge 174, which terminates at a horizontal clipping surface 176. When the paddle is to be placed on post 34, spring clips 168 and 170 will be moved into slot 144 and as the paddle is moved upwardly the bevelled surfaces 174 will slide around the curved lower edge 145 with the spring clips 168 and 170 yielding outwardly. As the spring clips move upwardly along sidewalls 147 surfaces 176 will reach ledges 148 and will snap into place thereon. In this way a simple but effective securing arrangement will be provided between paddle 36 and post 34.

As will be noted from FIG. 16, an angle is formed between each of the paddles 160 and 162 and the spring members 168 and 170 that extend there between. A similar angle will be developed between each paddle and post 34 following the mating of those elements. This angle together with the flat, large smooth surfaces of each paddle are important in order to provide the proper upward lifting and downward pushing mixing strokes which are preferably developed in an alternating way. For example, the paddles may be first turned in one direction and then rotated in the reverse direction. This not only provides better mixing but also moves the mixing components to expose incorporated air and produces the desired surface exposure within the components during mixing. This angle is shown at "A" in FIG. 16, with that angle being preferably 32° with the angle range being from about 30°, to about 34°.

When the paddle is rotated in a counter clockwise direction the upwardly facing surface of each blade will engage the mixture lifting the mixture and allowing it to flow upwardly toward the top curved edge. We have found that the uppermost portion of each paddle blade should extend above the admixed components regardless of the volume within the mixing vessel. Then as the mixture flows over the top and/or outer edges, the mixed material will break over that top edge exposing and breaking open incorporated bubbles, with the exposed surface being greatly increased.

When the paddle is rotated in a clockwise direction the downwardly facing surfaces of each blade will engage the mixture forcing the mixture downwardly toward the bottom of the mixing vessel then outwardly toward and upwardly along the outer surfaces of the vessel and between those surfaces and the outer peripheral surfaces of the blades. This also creates large exposed surface areas within the mixture.

The mixing paddle 36 is preferably comprised of thin, stainless steel, the thickness being about 0.030 inches.

The height of the paddle blade from lobe 166 to the top of the paddles is approximately 2.147 inches with the width from side to side being about 2.52 inches. In the finished blade the opening formed at 172 has a height below edges 176 of about 0.444 inches with the spring clips 170 and 172 housing a length of about 0.637 inches. The spacing between each paddle and the adjacent spring clip is about 0.040 inches with edges 176 having a length of about 0.016 inches. The spacing between the interior edges of the paddles is about 0.330 inches. While it is preferred that the paddle be made out of stainless steel, what is important is that the paddle not be bulky but formed from relatively thin yet very stiff material that can be either bent into or formed into the appropriately angled shape as shown. Thus, the paddle could be formed from a very hard plastic, thermal set resin or other suitable man made material so that suitable blade size and strength together with the desired relatively small cross-sectional thickness could be achieved. It is important to note that this blade structure, unlike prior art structures which tended to stir materials in an upward direction, will cause stirring to continue in a variety of directions ahead of each of the paddles 160 and 162 in the direction of their rotation and rotationally relative to the outside of mixing chamber. The outer edges of blades 36 are preferably curved and become progressively more curved from bottom to top so that the edges become spaced farther from the interior of the mixing chamber walls adjacent the upper portion of the paddles with stirrer 38 extending downwardly along the sidewall to continuously scrape the upper portion of the mixing chamber sidewall as post 34 is rotated. As was mentioned above, this paddle structure will create large exposed surface areas within the mixture, adjacent the outer peripheral edge of each paddle. During paddle rotation, this serves to continuously expose embedded gas bubbles to an open or exposed surface, allowing them to be broken and the gas therein released. Additionally, the rotational flow established by the rotation of the paddles effectively creates a central vortex type of counter current rotating flow with movement of the mixture being either upwardly or downwardly depending upon paddle rotation and along the walls of the vessel and either toward or away from post 34.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed:

1. A device for mixing liquid and dry components and for removing entrapped air from within the dry component as well as vaporous and gaseous effluents from the admixed components during mixing to produce a substantially pore free material comprising:
   a mixing-reaction vessel and a removable cover assembly for sealing said mixing-reaction vessel;
   said mixing-reaction vessel including a reinforced, outer housing, a bottom closure and filter assembly, said outer housing having an inwardly extending upper edge from which an integrally formed mixing bowl depends, said mixing bowl being spaced inwardly from said outer housing thereby defining an evacuation chamber therebetween, said upper edge including means defining a plurality of spaced apart apertures to provide communication with said evacuation chamber, said outer housing including an exhaust port to provide external communication through said filter assembly into said evacuation chamber and through said apertures;
   a source of vacuum operatively connected to said mixing vessel;
   said cover assembly including a cover for closing said mixing bowl, a mixing device operationally associated with said cover so as to extend downwardly into said mixing bowl, and sealing means for producing a seal between said cover and about said upper edge radially outwardly of said plurality of apertures;
   said mixing device including a pair of oppositely angled mixing blades, each blade having solid, continuously extending flat exterior mixing surfaces and positioned at an angle ranging from about 30° to about 34° downwardly from vertical and having an exterior edge the major portion of which is shaped to substantially conform to the interior shape of the mixing bowl, said mixing blades combining to extend across substantially the entire interior dimension of the mixing bowl, said mixing device also including scraping means for scraping the upper portions of the mixing-reaction vessel, whereby rotation of the mixing device will produce mixing forces on the components which mix the components in a generally vertical direction and simultaneously establishes large exposed surfaces within said component mix as said mixing device is operated so that air entrained within the dry components and the mixture as well as other vaporous and gaseous pockets within the mixture are exposed and ruptured.

2. A device as in claim 1 wherein said mixing device is mounted so as to allow rotation establishing counter current rotational mixing forces in the mixing components.

3. A device as in claim 1 wherein the blades are positioned at an angle of about 32° from vertical.

4. A device as in claim wherein the dry component is comprised of an air-fluffed powder.

5. A device as in claim 1 wherein the exterior edge of the mixing blades become progressively more curved from bottom to top so that the exterior edges become spaced farther from the interior of the mixing chamber interior adjacent the upper portions of the mixing blades.

6. A device as in claim 1, wherein each of said mixing blades further includes a substantially straight interior edge extending upwardly from a point adjacent a bottom end of said shaft but spaced outwardly therefrom whereby rotation of the blades creates vertical movement of the components in the interior and central portions of the mixing chamber and circulating movement adjacent the outer portions of the mixing chamber.

7. A device for mixing components under controlled vacuum conditions and in a manner that will remove entrapped air and other vaporous and gaseous effluent comprising a housing assembly, a cover assembly for sealingly enclosing said housing assembly, said housing assembly including means defining a mixing chamber, a source of vacuum operatively connected to said mixing chamber, said cover assembly including a mixing assembly comprised of a shaft rotatably secured within said cover assembly and a pair of oppositely angled mixing blades, each of said mixing blades being positioned at an angle of about 30° to 34° from vertical and having continuously extending solid surfaces, said mixing assembly further including scraping means spaced from said mixing blades for scraping the upper portion of said mixing chamber, said mixing blades and scraping means being secured to said shaft so as to rotate within said mixer to thereby effect the movement of the components within said mixing chamber, said mixing blades being characterized by each blade having an exterior edge that substantially conforms to the interior shape of the mixing chamber along a major portion of that exterior edge and positioned relative to said shaft and mixing chamber so as to extend therebetween so that a major portion of the exterior edge of each blade lies substantially adjacent the interior surface of the mixing chamber, said mixing blades combining to extend across substantially the entire interior dimension of the mixing bowl, each blade having a substantially straight interior edge extending upwardly from a point adjacent a bottom end of said shaft but spaced outwardly therefrom whereby rotation of the blades creates vertical movement of the components in the interior and central portions of the mixing chamber and circulating movement adjacent the outer portions of the mixing chamber.

8. A device as in claim 7 wherein said mixing blades are each positioned at an angle of about 32° from vertical.

9. A device as in claim 7 wherein the mixing blades are formed from a stiff material and have a substantially uniform thickness of about 0.030 inches.

10. A device as in claim 9 wherein the mixing blades each have substantially flat front and rear faces.

11. A device as in claim 7 wherein the mixing blades are comprised of rigid material.

12. A device as in claim 11 wherein the rigid mixing blades are comprised of metal.

13. A device as in claim 11 wherein the rigid mixing blades are comprised of plastic.

14. A device as in claim 7 wherein said scraping means is in the form of an L-shaped wire member secured to said shaft as to extend outwardly to the housing defining said mixing chamber.

15. A device as in claim 7 further including an absorptive gas filter provided within the operative connection between the mixing chamber and said vacuum source.

16. A device as in claim 7 wherein the mixing chamber is dish shaped having a curved bottom wall portion, a curved lower side wall portion extending outwardly and upwardly from the curved bottom wall portion and a substantially vertical upper side wall portion extending upwardly from said lower side wall portion.

17. A device as in claim 16 wherein said mixing blade has a curved outer peripheral edge.

18. A device for mixing orthopedic cement components comprised of a housing, a mixing vessel defined by interior and exterior walls attached to said housing so at least a portion of the exterior wall is spaced internally of said housing, aperture means for connecting the interior of said vessel and the portion between the housing and the exterior walls of said vessel together, said mixing vessel is dish shaped having a curved bottom wall portion, a curved lower sidewall portion extending outwardly and upwardly from the curved bottom wall portion and a substantially vertical upper sidewall portion extending upwardly from said lower sidewall portion, a cover for sealing said mixing vessel, a mixing assembly rotatably secured to said cover, said mixing assembly having a shaft, a handle attached to one end of the shaft and a pair of solid blade members secured to the other end of said shaft at oppositely directed angular relationship to said shaft ranging from about 30° to 34° with respect thereto, said blade members having peripheral exterior edge portions that lie directly adjacent the interior surfaces of the vessel at the bottom thereof and progressively curve away from the interior walls along the vertically extending portions thereof, and a source of vacuum operatably connected to the mixing vessel.

19. A device as in claim 18, wherein each of said solid blade members further includes a substantially straight interior edge extending upwardly from a point adjacent a bottom end of said shaft but spaced outwardly therefrom whereby rotation of the blades creates vertical movement of the components in the interior and central portions of the mixing chamber and circulating movement adjacent the outer portions of the mixing chamber.

* * * * *

UNITED STATES PATENT AND TRADEMARK OFFICE
CERTIFICATE OF CORRECTION

PATENT NO. : 4,961,647

DATED : October 9, 1990

INVENTOR(S) : Garry D. Coutts et al

It is certified that error appears in the above-identified patent and that said Letters Patent is hereby corrected as shown below:

Column 10 Line 43, insert --1-- after the word "claim"

Signed and Sealed this

Twenty-fifth Day of August, 1992

Attest:

DOUGLAS B. COMER

*Attesting Officer*   *Acting Commissioner of Patents and Trademarks*